(12) United States Patent
Hamada

(10) Patent No.: US 7,321,030 B2
(45) Date of Patent: Jan. 22, 2008

(54) TUMOR-SPECIFIC PROMOTOR AND USE THEREOF

(75) Inventor: Katsuyuki Hamada, Matsuyama (JP)

(73) Assignee: The New Industry Research Organization, Hyogo (JP)

( * ) Notice: Subject to any disclaimer, the term of this patent is extended or adjusted under 35 U.S.C. 154(b) by 0 days.

(21) Appl. No.: 10/489,258

(22) PCT Filed: Jan. 30, 2002

(86) PCT No.: PCT/JP02/00724

§ 371 (c)(1),
(2), (4) Date: Oct. 4, 2004

(87) PCT Pub. No.: WO03/025190

PCT Pub. Date: Mar. 27, 2003

(65) Prior Publication Data

US 2005/0031591 A1 Feb. 10, 2005

(30) Foreign Application Priority Data

Sep. 14, 2001 (JP) .............................. 2001-279088

(51) Int. Cl.
*C07H 21/04* (2006.01)
*C12N 15/36* (2006.01)

(52) U.S. Cl. ................... 536/24.1; 435/320.1; 435/325

(58) Field of Classification Search ............... 536/23.1, 536/24.1, 25.3, 25.1, 5; 435/5; 514/44
See application file for complete search history.

(56) References Cited

FOREIGN PATENT DOCUMENTS

WO       WO 98/23779 A1      6/1998

OTHER PUBLICATIONS

Barker et al. Genomics 1996, vol. 38 (2), pp. 215-222.*
David F. Barker, et al., "The BRCA1 and 1A1. 3B Promoters Are Parallel Elements of a Genomic Duplication at 17q21," Genomics, Dec. 1996, pp. 215-222, vol. 38, No. 2.
Carla Heise, et al., "Replication-selective adenoviruses as oncolytic agents," The Journal of Clinical Investigation , Apr. 2000, pp. 847-851, vol. 105, No. 7.

* cited by examiner

*Primary Examiner*—Bruce R. Campell
*Assistant Examiner*—Bao Qun Li
(74) *Attorney, Agent, or Firm*—Sughrue Mion, PLLC

(57) ABSTRACT

A promoter domain of 1816 bp or 441 bp in the upstream side of exon 1B of IAI.3B gene has a specifically high promoter activity in ovarian cancer cells. An adenovirus having this promoter domain inserted in the E1 domain thereof exhibits a specifically high cell proliferation inhibitory effect on ovarian cancer cells. Thus, it is efficacious in gene therapy for ovarian cancer.

3 Claims, 12 Drawing Sheets

CYTOTOXIC ACTIVITY OF ONCOLYSTIC ADENOVIRUS Ad-IAI.3B-1816 VARIOUS CELL LINES

IN VIVO ANTI-TUMOR ACTIVITY OF ONCOLYSTIC ADENOVIRUS Ad-IAI.3B-1816

IN VIVO ANTI-TUMOR ACTIVITY OF ONCOLYSTIC
ADENOVIRUS Ad-IAI.3B-1816

Ad-IAI.3B-1861
ADMINISTRATION
GROUP

CONTROL GROUP

TUMOR-SPECIFIC PROMOTOR AND USE THEREOF

TECHNICAL FIELD

The present invention relates to a tumor-specific promoter that permits the expression of specific genes in tumor cells or tumor tissues such as ovarian cancer and uses thereof. More specifically, it relates to a tumor-specific promoter that exhibits a specifically high promoter activity in tumor cells or tumor tissues, specifically in ovarian cancer cells or ovarian cancer tissues, and that permits the gene therapy of cancers, specifically ovarian cancer, by a tumor-specific gene expression, and a cytotoxic tumor-specific virus in which a virus gene has been altered using said tumor-specific promoter so that the virus can proliferate specifically in tumor cells or tumor tissues, specifically ovarian cancer cells or ovarian cancer tissues. Furthermore, the present invention relates to a method of treating cancers using this cytotoxic tumor-specific virus.

BACKGROUND ART

In Europe and the United States, ovarian cancer has been considered one of the five major cancers. In Japan, ovarian cancer kills about 4,000 people every year, and the number of casualties have rapidly increased by about 30-fold in the last 40 years, and it is one of the cancers most growing in number together with lung cancer and pancreatic cancer. Since ovarian cancer is present in the abdominal cavity, is difficult to diagnose early, and the capsule of ovarian cancer is easily broken and thus tends to metastasize early to the abdominal cavity, 60% of the patients die eventually, and thus it is one of the cancers having bad prognosis together with pancreatic cancer. Improved performance in therapy has been recognized due to the development of surgical methods and anti-cancer agents such as cisplatin and taxol, but none of the subsequent improvements in therapeutic regimens have been effective, and thus there is a need for the development of a new therapeutic method.

Recently, gene therapy has been tested in various cancers in which tumor suppressor genes, cytokine genes etc. are introduced into cancer cells to treat cancers, and its clinical usefulness has been confirmed. In ovarian cancer as well, it was found, gene therapy with a tumor suppressor gene p53 using an adenovirus vector exhibits clinical usefulness (reduction of tumor by 50% or more) in over 20% of recurrent ovarian cancers that did not respond to treatment with cisplatin or taxol (J. K. Wolf et al., Proceedings of American Society of Clinical Oncology, Vol. 19, May 2001, 382). Furthermore, oncolytic adenovirus has been developed aiming at the effect of cell lysis by adenovirus against tumor cells, and its usefulness has been confirmed in various cancers (Carla Heise et al., The Journal of Clinical Investigation, April 2000, Vol. 105, No. 7, 847-851; James R. Bischoff et al., Science, Vol. 274, 18 Oct. 1996, 373-376; J. Nemunaitis et al., Journal of Clinical Oncology, Vol. 19, No. 2, 2001, 289-298). Also, cell lysis effect by an oncolystic herpes virus using herpes virus has been reported (Miyatake S, et al., Gene Ther. 1999, Vol. 6, 564-572). However, with regard to virus vectors for use in such gene therapy, virus promoters such as CMV and RSV have conventionally been used, but an improved effect was not expected because the dose was limited due to the lack of tissue-specificity and hence to toxicity to the liver etc.

Gene therapy with vectors using organ-specific promoters is also being developed. Thus, clinical trials are about to start, for example, for gene therapy of bone metastasis of prostate cancer by a vector using an osteocalcin promoter (Shirakawa et al., Cancer Gene Therapy, 1998 September-October, 1998, 5(5), 274-280, 1998), for gene therapy of hemophilia by a vector using an albumin promoter (Alemany et al., J. Virol. Methods, 1997 November 68(2): 147-159), and for gene therapy of prostate cancer by a vector using a PSA promoter (Gotoh et al., J. Urol.1998 July 160(1): 220-229). However, no reports have been made on gene therapy using an ovarian cancer-specific gene promoter.

On the other hand, the IAI.3B gene has been reported as a gene purified and cloned by screening a cDNA library of an ovarian cancer cell line OVCA432 using an antibody generated in rabbits immunized with, as antigen, a protein in the high molecular weight region that abounds in the protein fraction specific to ovarian cancer in the pleural effusion of metastatic ovarian cancer (Campbell I. G., et al., Human Molecular Genetics, 1994, Vol. 3, No. 4, 589-594). It has also been reported that the open reading frame of the IAI.3B gene is 2990 bp, and the amino acid sequence of the protein encoded thereby comprises 966 amino acids with a molecular weight of 108 kd, that the protein encoded by the IAI.3B gene is a B-box protein having a transformation potential and the genomic gene is located in the telomere in the vicinity of the BRCA1 gene which is a tumor suppressor gene of ovarian cancer and breast cancer located at chromosome 17q21.1 (Campbell I. G., et al., Human Molecular Genetics, 1994, Vol. 3, No. 4, 589-594). It has also been suggested that the IAI.3B gene and the BRCA1 gene share the promoter region and the enhancer region (Melissa A. Brown et al., Nature, Vol. 372, 22/29 December 1994, 733), and that the regulatory mechanism of each gene expression plays an important role in the possible onset and proliferation of ovarian cancer (Melissa A. Brown et al., Oncogene, 1996, 12, 2507-2513). Though the activity of the promoter region of the BRCA1 gene has already been clarified (Smith et al., Genome Res., 1996 November; 6(11): 1029-1049), no reports have been made on the promoter activity of the IAI.3B gene.

DISCLOSURE OF THE INVENTION

If various virus vectors are constructed using tumor-specific promoters that specifically exhibit the promoter function in the ovarian cancer cells or the ovarian cancer tissues and gene therapy is performed using these virus vectors, it is specifically possible to permit the expression of the desired gene only in ovarian cancer, and thereby to attain reduced side effects and improved clinical effects that have been challenges in the conventional gene therapy.

Thus, it is an object of the present invention to provide a tumor-specific promoter that exhibits a specifically high promoter activity in tumor cells or tumor tissues, specifically in ovarian cancer cells or ovarian cancer tissues, and that permits the gene therapy of cancers, specifically ovarian cancer, by a tumor-specific gene expression.

It is another object of the present invention to provide a cytotoxic tumor-specific virus in which a virus gene has been altered using said tumor-specific promoter so that the virus can proliferate specifically in tumor cells or tumor tissues, specifically ovarian cancer cells or ovarian cancer tissues.

Furthermore, it is a further object of the present invention to provide a method of treating cancers using said cytotoxic tumor-specific virus.

In an attempt to clone the promoter region of the IAI.3B gene of which activity is expected to be enhanced in ovarian cancer, the present inventor has found that a gene that comprises the upstream region, specifically 1816 bp or 441 bp, of exon 1B of the IAI.3B gene and that has a base sequence at positions 1126-2941 or a base sequence at positions 2501-2941 set forth in SEQ ID NO: 1 of the sequence listing has a specifically high promoter activity specifically in ovarian cancer, and that it is useful as a promoter for constructing a cytotoxic tumor-specific virus, and thereby has completed the present invention.

Thus, the present invention relates to a tumor-specific promoter having a base sequence at positions 1126-2941 or a base sequence at positions 2501-2941 set forth in SEQ ID NO: 1 of the sequence listing.

The present invention further relates to a tumor-specific promoter that hybridizes under a stringent condition to a base sequence at positions 1126-2941 or a base sequence at positions 2501-2941 set forth in SEQ ID NO: 1 of the sequence listing, and that has a promoter function similar to that of those base sequences. Such a tumor-specific promoter preferably has a base sequence at positions 2626-2941, 2376-2941, 1251-2941, or 1001-2941 set forth in SEQ ID NO: 1 of the sequence listing. Preferably the above tumor-specific promoter is a promoter specific for ovarian cancer.

Furthermore, the present invention relates to a cytotoxic tumor-specific virus in which a virus gene has been altered using the above tumor-specific promoter so that the virus can proliferate specifically in tumor cells or tumor tissues. Preferably, the above cytotoxic tumor-specific virus of the present invention is specific for ovarian cancer. More preferably, the above cytotoxic tumor-specific virus is adenovirus.

Furthermore, the present invention relates to a method of treating cancers which comprises administering the above cytotoxic tumor-specific virus to humans. Preferably, it is a therapeutic method which comprises administering an anti-cancer chemotherapeutic agent in combination with the above cytotoxic tumor-specific virus.

BEST MODE FOR CARRYING OUT THE INVENTION

Figure 1:
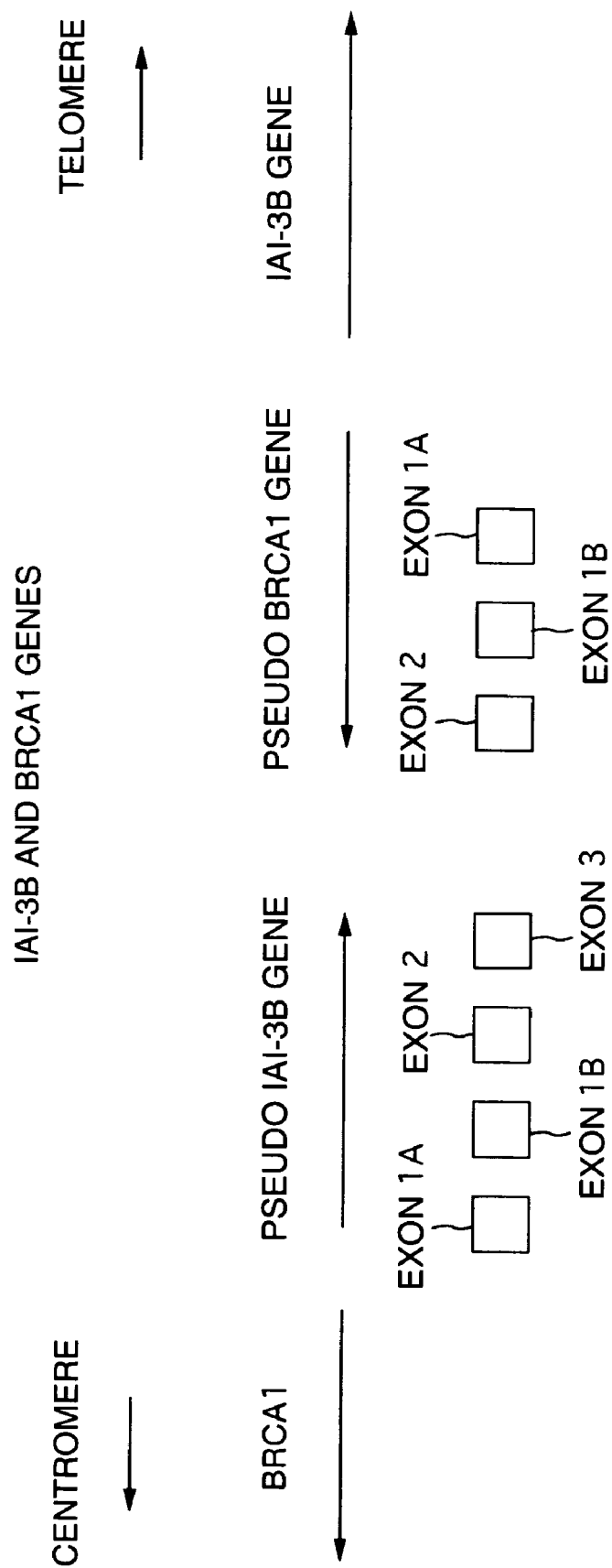
FIG. 1 is a drawing that shows a relationship between the IAI.3B genomic gene and the BRCA1 genomic gene.

The tumor-specific promoter of the present invention was obtained for the first time from a detailed study on the promoter region of the IAI.3B gene. As described above, the IAI.3B gene is a gene cloned by screening the cDNA library of an ovarian cancer cell line OVCA432 using an antibody raised against a protein in the high molecular weight region present in the pleural effusion of metastatic ovarian cancer. As shown in FIG. 1, the IAI.3B genomic gene is located in an antisense orientation in the telomere in the vicinity of the BRCA1 gene which is a tumor suppressor gene of ovarian cancer and breast cancer located at chromosome 17q21.1, and in between both genomic genes, the pseudo gene of each gene is present as promoter arranged in an antisense orientation. Thus, the promoter of the IAI.3B gene is exon 2, exon 1B and exon 1A of the pseudo gene of the BRCA1 gene arranged in an antisense orientation.

The tumor-specific promoter of the present invention comprises a base sequence at positions 1126-2941 or a base sequence at positions 2501-2941 set forth in SEQ ID NO: 1 of the sequence listing. The base at position 2941 of SEQ ID NO: 1 corresponds to a base located 1 bp upstream from the 5'-end of exon 1B of the IAI.3B gene. Thus, the tumor-specific promoter of the present invention comprising a base sequence at positions 1126-2941 or a base sequence at positions 2501-2941 set forth in SEQ ID NO: 1 of the sequence listing corresponds to a 1816 bp or a 441 bp base sequence, respectively, located upstream of exon 1B of the IAI.3B gene.

The tumor-specific promoter of the present invention may be a promoter comprising a base sequence that hybridizes under a stringent condition to a base sequence at positions 1126-2941 or a base sequence at positions 2501-2941 set forth in SEQ ID NO: 1 of the sequence listing, and that has a promoter function similar to that of those base sequences. As used herein "a base sequence that hybridizes under a stringent condition" means a base sequence that hybridizes to DNA having any of the above base sequences by Southern hybridization, for example, under a condition of reacting at 65° C. for 12 hours in a solution containing 6×SSE, 2 X Denhardt's solution, 0.5% SDS, and 0.1 mg/ml salmon sperm DNA. The tumor-specific promoter of the present invention is a base sequence that hybridizes under such a condition and that has a promoter function similar to the hybridized base sequence of interest, i.e. the same degree of tumor specificity and the same degree of promoter activity. As such base sequences, there can be mentioned base sequences having a homology of 60% or more, preferably 65% or more, with the hybridized base sequence of interest.

With regard to such a tumor-specific promoter of the present invention, as the one that hybridizes to a tumor-specific promoter comprising the base sequence at positions 1126-2941 set forth in SEQ ID NO: 1 of the sequence listing, there can be mentioned a tumor-specific promoter comprising the base sequence at positions 1251-2941 (1691 bp) or at positions 1001-2941 (1941 bp). As the one that hybridizes to a tumor-specific promoter comprising the base sequence at positions 2501-2941 set forth in SEQ ID NO: 1 of the sequence listing, there can be mentioned a tumor-specific promoter comprising the base sequence at positions 2626-2941 (316 bp) or at positions 2376-2941 (566 bp).

The above tumor-specific promoter of the present invention can be obtained by a known method that utilizes a PCR method based on a sequence information (Gene Bank Human 1A.3B gene, promoter region. ACCESSION U72843) already reported on the IAI.3B genomic gene. Such a method can be easily carried out by a person skilled in the art according to a basic textbook such as Molecular Cloning 2nd Ed., Cold Spring Harbor Laboratory Press (1989) and the like. The tumor-specific promoter of the present invention having a base sequence that hybridizes under the above stringent condition can be easily obtained by a method described above, or for example site-directed mutagenesis, a common hybridization method, and can be specifically carried out with reference to a basic textbook such as the above Molecular Cloning.

The above-mentioned tumor-specific promoter of the present invention has a high promoter activity, and a specifically high promoter activity in tumor cells or tumor tissues, specifically in ovarian cancer cells or ovarian cancer tissues. As has been demonstrated in Examples below, the tumor-specific promoter of the present invention comprising the base sequence at positions 1126-2941 (1816 bp) set forth in SEQ ID NO: 1 exhibits a promoter activity about 30 times that of the SV40 promoter in an ovarian cancer cell line HEY, and similarly the tumor-specific promoter of the present invention comprising the base sequence at positions 2501-2941 (441 bp) set forth in SEQ ID NO: 1 exhibits a promoter activity about 15 times as high. Also, the tumor-specific promoter of the present invention comprising the base sequence at positions 1126-2941 (1816 bp) set forth in SEQ ID NO: 1 exhibits a promoter activity about 2000 times that of the SV40 promoter in an ovarian cancer cell line PA-1, and about 70 times that of the SV40 promoter in another ovarian cancer cell line HRA, whereas in normal ovary cells NOE1, NOE2 and NOE3 it exhibits a promoter activity about 25% that of the SV40 promoter, and in a normal human keratinocyte cell line K42 it exhibits only about 20% that of the SV40 promoter. Therefore it exhibits a specifically high promoter activity in ovarian cancer. The tumor-specific promoter of the present invention comprising the base sequence at positions 2501-2941 (441 bp) set forth in SEQ ID NO: 1 also exhibits a specifically high promoter activity in ovarian cancer.

The tumor-specific promoter of the present invention can be used as a promoter for constructing a cytotoxic tumor-specific virus in which a virus gene has been altered so that the virus can be used in gene therapy of cancer based on cancer-specific gene expression, for example it can proliferate specifically in tumor cells or tumor tissues.

Such a cytotoxic tumor-specific virus is termed as the so-called oncolytic virus. Such a virus can be constructed by, for example, inserting the tumor-specific promoter of the present invention upstream of the early gene E1A or E1B, genes essential for the proliferation of adenovirus, or replacing the early gene E1A or E1B promoter, or by inserting the tumor-specific promoter of the present invention upstream of the corresponding early gene of herpes virus or replacing the early gene promoter. For retrovirus, reovirus and other viruses as well, the tumor-specific promoter of the present invention can be inserted or substituted to construct a cytotoxic tumor-specific virus. The cytotoxic tumor-specific virus thus constructed can exhibit the effect of specifically proliferating in tumor cells or tumor tissues and killing tumor cells. Thus, by administering this virus, ovarian cancer can be specifically treated with effect and with reduced side effects. For methods of constructing and using such a cytotoxic tumor-specific virus, reference is made to Carla Heise et al., The Journal of Clinical Investigation, April 2000, Vol. 105, No. 7, 847-851; James R. Bischoff et al., Science, Vol. 274, 18 Oct. 1996, 373-376; J. Nemunaitis et al., Journal of Clinical Oncology, Vol. 19, No. 2, 2001, 289-298, and the like.

Methods of administering the cytotoxic tumor-specific virus of the present invention to humans include an in vivo method in which said virus is directly introduced into a human or an ex vivo method in which certain cells and tissues are extracted from a human and said virus is introduced into said cells and tissues and the cells and tissues are returned to the human. In the in vivo method, for example, after the cytotoxic tumor-specific virus of the present invention has been dissolved in a suitable solvent (a buffer such as PBS, physiological saline, sterile water, etc.), it is filter-sterilized as needed, and then aseptically filled into sterile containers to prepare injections, which are administered to humans by injection. Conventional carriers may be added into the injections as needed. The cytotoxic tumor-specific virus of the present invention can be administered intravenously, intramuscularly, intraperitoneally, subcutaneously or the like, and can be directly administered to tumor tissues. In the ex vivo method, the cytotoxic tumor-specific virus of the present invention is directly injected to tissues in injections similar to those mentioned above, which is then returned to a human body (The Japan Society of Gene Therapy ed., Handbook for Development and Research of Gene Therapy, NTS, 1999).

The dosage of the cytotoxic tumor-specific virus of the present invention may vary depending on the subject to be administered, the method of administration, the dosage form etc., but is usually in the range of $1 \times 10^9$-$1 \times 10^{14}$ virus particles per adult human, preferably $1 \times 10^{10}$-$1 \times 10^{13}$ virus particles.

The cytotoxic tumor-specific virus of the present invention may be used in combination with anti-cancer agents commonly used in clinical practices. Combined use can result in synergism in anti-cancer effect, and can reduce the dosage of both agents, leading to reduced side effect and enhanced anti-cancer effect. Anti-cancer chemotherapeutic agents are preferably alkylating agents such as cisplatin and cyclophosphamide; antimetablites such as methotrexate, mercaptopurine and cytosine arabinoside; anti-cancer antibiotics such as actinomycin and adriamycin; plant alkaloids such as etoposide, taxol, vincristine and vinblastine; immunological agents such as picibanil and krestin; DNA topoisomerase inhibitors such as irinotecan and topotecan, and the like. Among them, cisplatin, cyclophosphamide, adriamycin, etoposide and taxol are preferred.

Furthermore, the tumor-specific promoter of the present invention can also be used in a suicide gene therapy in which the gene of a drug metabolic enzyme and a prodrug for cancer therapy are combined, and in an immunological gene therapy in which a cytokine gene is introduced into cancer cells to enhance immunological function and thereby to treat cancer.

With regard to the suicide gene therapy, examples of combination of gene of a drug metabolic enzyme and a prodrug for cancer therapy include the combination of the gene of herpes simplex virus thymidine kinase and gancyclovir or acyclovir, cytosine deaminase gene and 5-fluorocytosine, the gene of varicella-zoster virus thymidine kinase and 6-methoxypurine arabinoside, *E. coli* gpt gene and 6-thioxanthine, cytochrome P450 2B1 gene and cyclophosphamide, human deoxycytidine kinase gene and cytosine arabinoside, *E. coli* UPRT gene and 5-fluorouracil, *E. coli* deoD gene and 6-methylpurine-2'-deoxyribonucleoside, or the like. In actually conducting a suicide gene therapy, an expression vector in which the tumor-specific promoter of the present invention and the gene of a drug metabolic enzyme integrated upstream thereof in such a way as to permit expression is constructed, the expression vector is introduced into cancer cells, and then a prodrug for cancer therapy is administered. As vectors, there can be mentioned vectors commonly used for gene introduction such as retrovirus vector, adenovirus vector and adeno-associated virus. Alternatively, a plasmid DNA in which the tumor-specific promoter of the present invention and the gene of a drug metabolic enzyme integrated downstream thereof in such a way as to permit expression may be introduced into cancer cells by enclosing it in a liposome or as a polylysine-DNA-protein complex. It can also be introduced into cancer cells in the form of naked plasmid. In order to introduce genes, these vectors, liposomes etc. are injected intravenously or intraarterially, or directly into tumor or the periphery of tumor. At this time, electroporation or ultrasound may be used in combination to enhance gene transfer efficiency. After gene introduction, a prodrug for cancer therapy may be administered in a standard method of oral, intravenous, intaarterial administration etc.

The introduced gene undergoes the effect of the tumor-specific promoter of the present invention and expresses the drug metabolic enzyme specifically in cancer cells, and via the expressed drug metabolic enzyme, the prodrug for cancer therapy is converted to a cancer therapy agent in an active form in cancer cells, which converted cancer therapy agent selectively kills cancer cells to complete the suicide gene therapy.

The technique per se of such a suicide gene therapy is known, and the combination of the gene of herpes simplex virus thymidine kinase and gancyclovir has been put into clinical use as in brain tumor (Oldfield, E H, Hum. Gene Ther., 4, 39-69, 1993), and the combination of the cytosine deaminase gene and 5-fluorocytosine has been suggested in potential clinical use in colon cancer etc. (Huber, B E et al., Cancer Res., 53, 4619-4626, 1993), and these examples are referred to in conducting the gene therapy of the present invention.

With regard to an immunological gene therapy that utilizes the tumor-specific promoter of the present invention, a gene encoding a cytokine such as interferon, TNF-α and interleukin is integrated into an expression vector together with the tumor-specific promoter of the present invention in a method similar to the suicide gene therapy mentioned above, or enclosed into liposomes, or introduced into cancer cells in the form of naked plasmid. A method of treating cancer is adopted in which it is introduced into cancer cells to express the cytokine and thereby to enhance immune response, a biological defense mechanism inherently borne by humans, to treat cancer.

Also, using the tumor-specific promoter of the present invention, an antisense gene of an oncogene or a normal type tumor suppressor gene may be specifically expressed in tumor, which can result in the induction of decanceration (normal return) of tumor and cell death (apoptosis), and further the induction of enhanced sensitivity of tumor cells to anti-cancer agents or to radiation. The tumor-specific promoter of the present invention can also be inserted together with the above-mentioned gene encoding a cytokine etc. at the E1 deletion site to construct a E1-deleted, E1/E3-deleted adenovirus vector, which is then used in commonly practiced gene therapy.

Gene therapy using the tumor-specific promoter of the present invention is specifically useful for the treatment of ovarian cancer.

Hereinafter, the present invention will be explained in more detail with reference to Examples, but it should be noted that the present invention is not limited by the scope of these Examples in any way.

EXAMPLE 1

Cloning of a Tumor-Specific Promoter in the IAI.3B Gene (1) Experimental Method

Exon 1 of IAI.3B and 160 bp upstream thereof were used in a PCR method to create a DNA template, based on which, a single clone (pCA1) was isolated from the EMBL3 SP6/T7 phage library of Clontech, and it was confirmed by PCR that exon 1 of IAI.3B and 160 bp upstream thereof have been contained. The experiment used ovarian cancer cell lines PA-1, HRA, HEY, normal human ovary cells NOE1, NOE2 and NOE3, a cervical cancer cell line SKGIIIA, and a normal human keratinocyte cell line K42. Specifically the experiment was carried out as follows:

1. The transcription initiation point (Cap site) was determined using the SMART PCR cDNA synthesis kit (Clontech).

Figure 2:
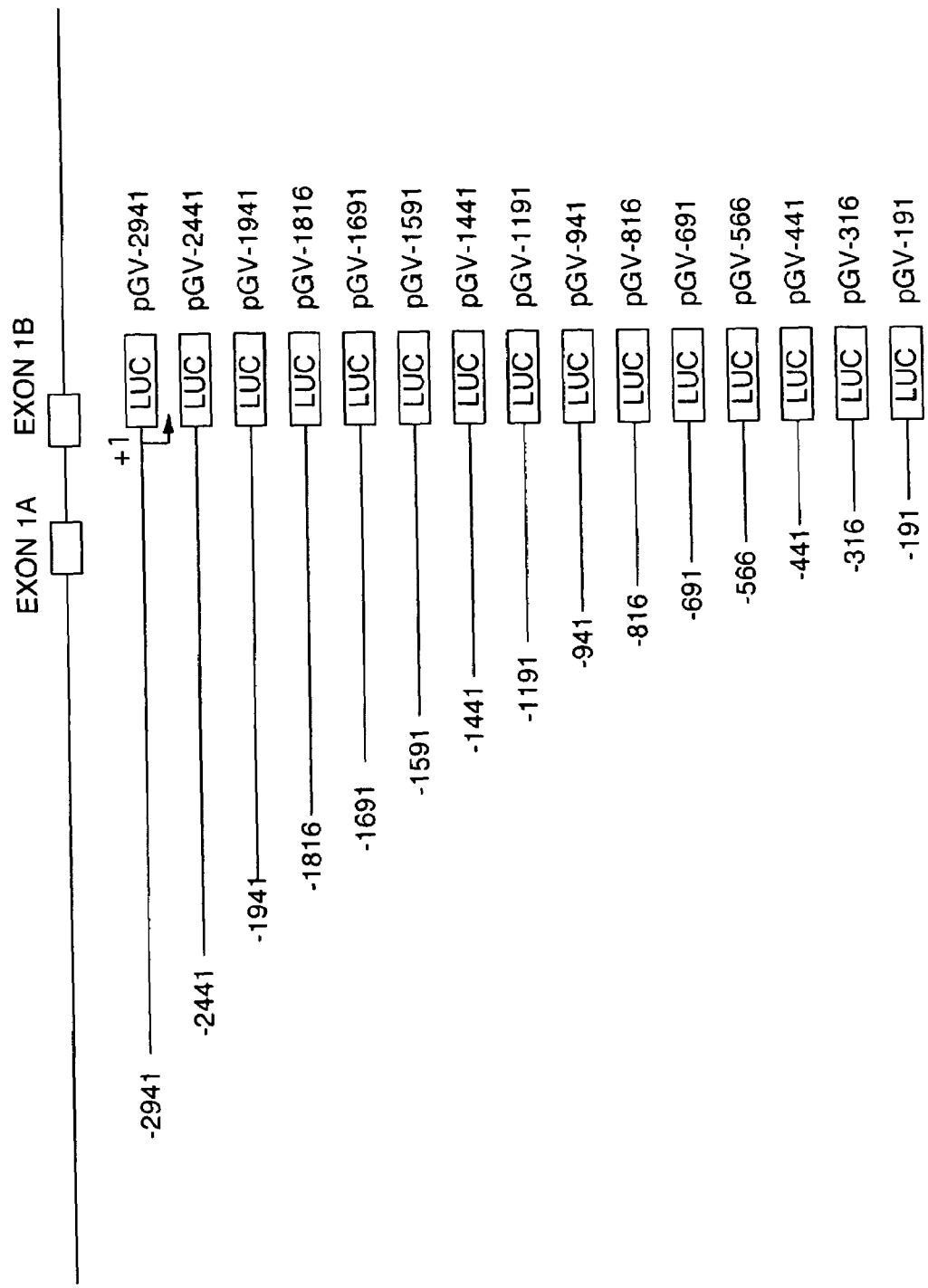
FIG. 2 is a drawing that shows a relationship between each deletion mutant of the promoter region of the IAI.3B gene and luciferase vectors having them inserted therein.

2. By setting an antisense primer at exon 1B and setting a sense primer at every 50-500 bp, a PCR product of the upstream side of exon 1B was created, which was integrated into the restriction sites of restriction enzymes Mlu I and BglII of luciferase vector (PicaGene vector, Toyo Ink). Furthermore, using the dual luciferase assay kit (Promega), the deletion mutants which are PCR products were subjected to luciferase assay to identify promoter activity. The relationship of each deletion mutant and a luciferase vector obtained by integrating it is shown in FIG. 2. In FIG. 2, the luciferase vector pGV-2941, for example, has integrated therein a deletion mutant comprising a 2941 bp base sequence at positions 1-2941 set forth in SEQ ID NO: 1. Similarly, pGV-1941, pGV-1816, pGV-1691, pGV-566, pGV-441 and pGV-316 have integrated therein a deletion mutant comprising, respectively, a 1941 bp base sequence at positions 1001-2941, a 1816 bp base sequence at positions 1126-2941, a 1691 bp base sequence at positions 1251-2941, a 566 bp base sequence at positions 2376-2941, a 441 bp base sequence at positions 2501-2941 and a 316 bp base sequence at positions 2626-2941.

3. In order to confirm the absence of mutation for each deletion mutant obtained by PCR and inserted into each luciferase vector, sequencing was performed by an automated DNA sequencer (ABI 310; Applied Biosystems).

4. Luciferase vectors containing each promoter region determined in the above experiment were compared, for the organ-specific gene expression to ovarian cancer, with conventional promoters (SV40 promoter, CMV promoter).

(2) Results

The transcription initiation point was found to be exon 1B, and the conventionally reported exon 1B (Brown, M A et al., Oncogene, 12: 2507-2513, 1996) was revealed to start at 3 bp further upstream. Also, the conventionally reported exon 1A (Brown, M A et al., Oncogene, 12: 2507-2513, 1996) was found not to be transcribed.

Figure 3:
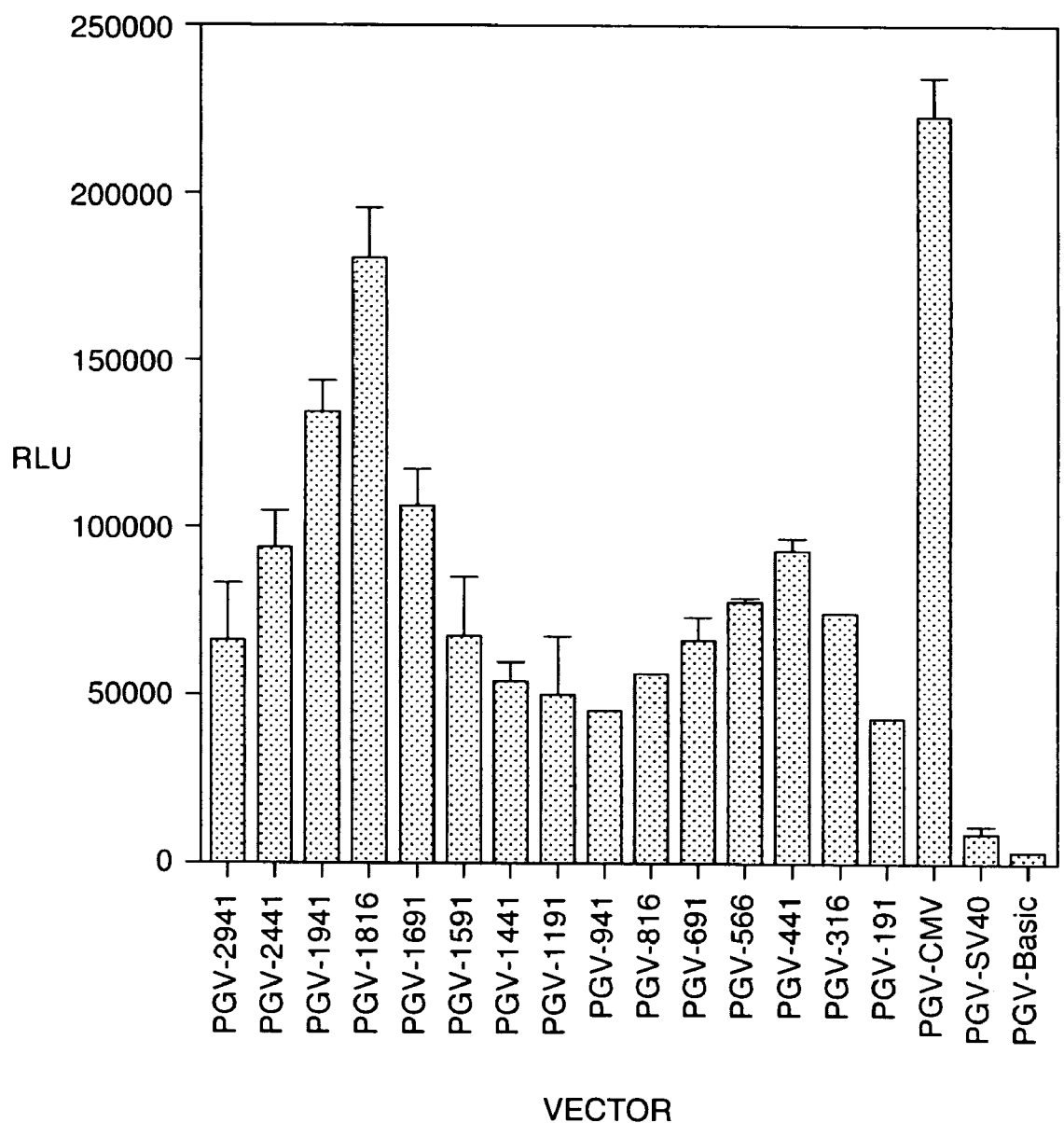
FIG. 3 is a graph showing a promoter activity in luciferase vectors having inserted therein each deletion mutant of the promoter region of the IAI.3B gene.

The result of measurement of promoter activity by the dual luciferase assay for luciferase vectors (FIG. 2) created by integrating each deletion mutant at positions 191 bp to 2941 bp in the 5' upstream region of exon 1B demonstrates that the highest promoter activity lies at the 1815 bp upstream region as shown in FIG. 3. Promoter activity of deletion mutants at the downstream region begins to decrease gradually and becomes lowest at pGV-941, indicating the presence of a positive element in between 1691 bp and 941 bp. Furthermore, when compared to the promoter activity of deletion mutants in the downstream region, each activity started to increase reaching the highest value at pGV-441. This revealed that there is a negative element at 816 bp to 441 bp. When further compared to deletion mutants in the downstream region, promoter started to decrease indicating that there is a positive element in the region downstream from 316 bp.

Furthermore, as shown in FIG. 3, it was revealed that pGV-1816 exhibits a promoter activity about 30 times that of the pGV-control, the SV40 promoter, in an ovarian cancer cell line HEY, and a very high activity of about 80% as compared to PGV-CMV, the CMV promoter.

Figure 4:
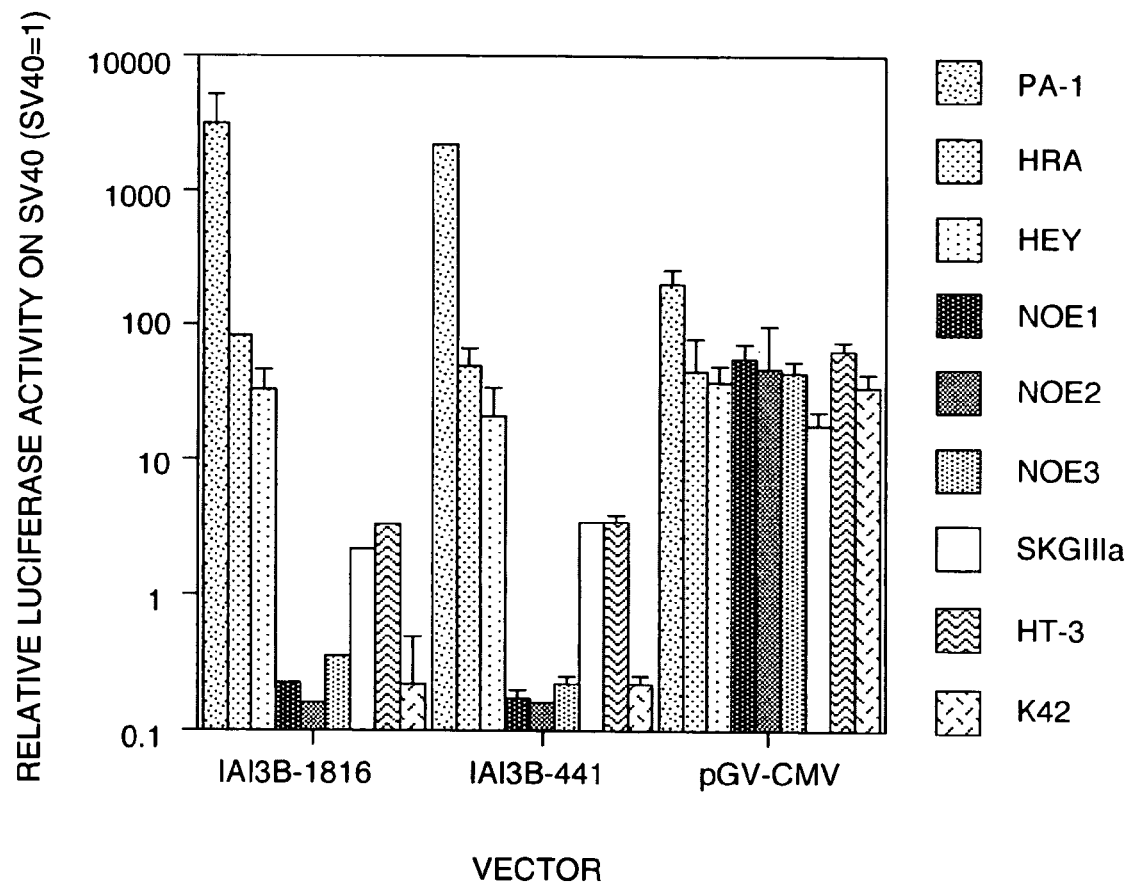
FIG. 4 is a graph showing a promoter activity in each cell line of luciferase vectors having inserted therein a 1816 bp and a 441 bp deletion mutant of the promoter region of the IAI.3B gene.

Furthermore, as shown in FIG. 4, in another ovarian cancer cell line PA-1, the highest activity was in pGV-1816 and the value was about 2000 times that of the SV40 promoter and about twice that of the CMV promoter. Also, in another ovarian cancer cell line HRA, the highest activity was in pGV-1816 and the value was about 70 times that of the SV40 promoter and about twice that of the CMV promoter. In a cervical cancer cell line SKGIIIA, the promoter activity of pGV-1816 was about five times that of the SV40 promoter and 13% that of the CMV promoter. In another cervical cancer cell line HT3, the promoter activity of pGV-1816 was about three times that of the SV40 promoter and 5% that of the CMV promoter. On the other hand, in the normal human ovary cells NOE1, NOE2 and NOE3, the promoter activity of pGV-1816 was about 25% that of the SV40 promoter and 0.25% that of the CMV promoter. Furthermore, in a normal human keratinocyte cell line K42 as well, the promoter activity of pGV-1816 was about 20% that of the SV40 promoter and 0.7% that of the CMV promoter.

From the foregoing, the IAI.3B gene promoter had a high specificity for ovarian cancer with the values at 80% to two times that of the CMV promoter. Furthermore, the high activity was also noted in cervical cancer cell lines as well with the values at about two to three times that of the CMV promoter. On the other hand, in normal ovary cells and keratinocytes, the activity was low with the values at about 20% to 30% that of the CMV promoter.

EXAMPLE 2

The Transcription Activity of the IAI.3B Gene Promoter

Figure 5:
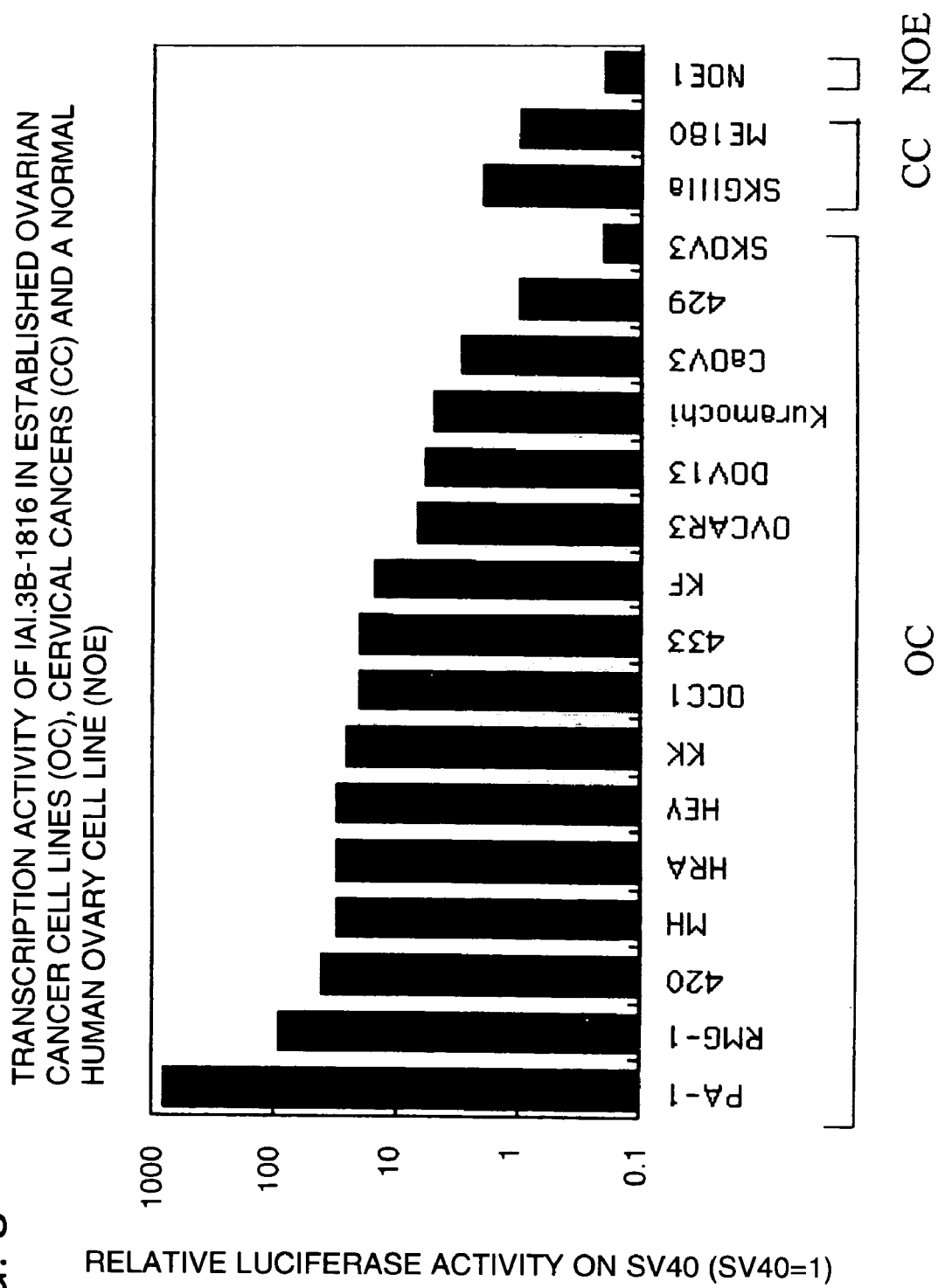
FIG. 5 is a graph that compares the transcription activity of promoter IAI.3B-1816 in established ovarian cancer cell lines (OC) and those of cervical cancers (CC) and of a normal human ovary cell line (NOE).
Figure 6:
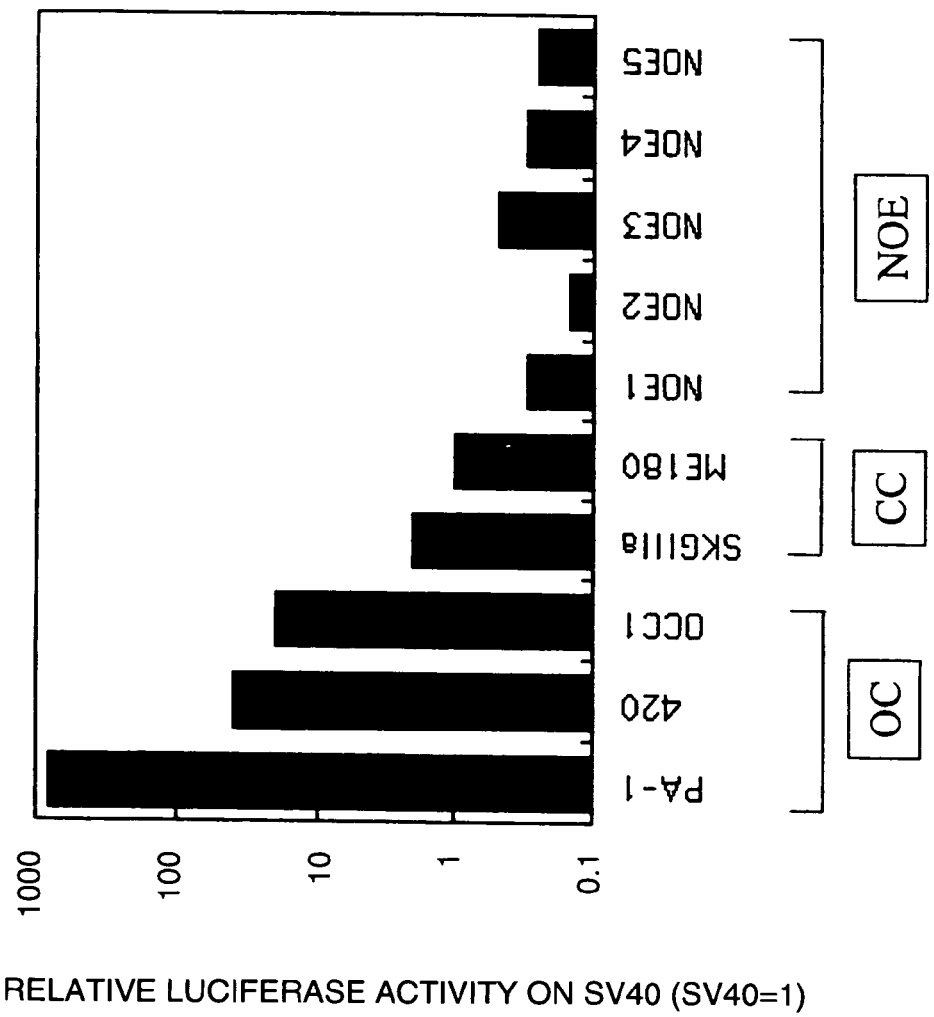
FIG. 6 is a graph that compares the transcription activity of promoter IAI.3B-1816 in established ovarian cancer cell lines (OC) and those of cervical cancers (CC) and of normal human ovary cell lines (NOE).
Figure 7:
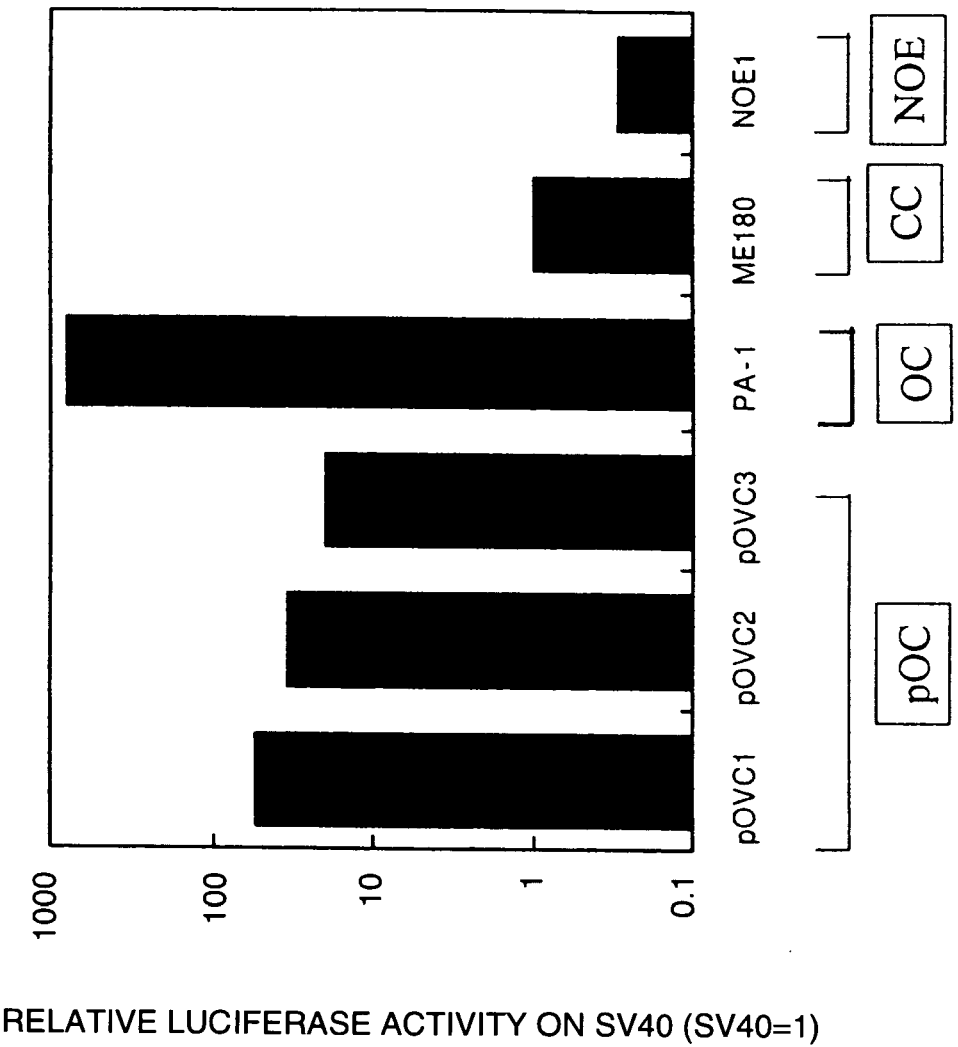
FIG. 7 is a graph that compares the transcription activity of promoter IAI.3B-1816 in primary cultured ovarian cancer cell lines (pOC) and those of cervical cancers (CC) and of normal human ovary cell lines (NOE).

In almost the same manner as the method described in (1) 2 of Example 1, the dual luciferase method was used to determine the transcription activity of Ad-IAI.3B-1816 in established ovarian cancer cell lines (OC) and primary cultured ovarian cancer cell lines (pOC). As controls, cervical cancer cell lines (CC) and normal ovary cell lines (NOE) were used. Specifically, a luciferase vector pGV-1816 containing promoter IAI.3B-1816 comprising a 1816 bp base sequence at positions 1126-2941 set forth in SEQ ID NO: 1 constructed in (1) 2 of Example 1 and the RL-TK vector as a control were mixed at a ratio of 10:1, which was allowed to bind to the DOTAP liposome reagent, and then added together with a culture liquid without added fetal calf serum to each well of a 12-well plate for cell culture to which each cell had been plated, cultured for two days, and firefly luciferase and then sea kidney luciferase were determined using a lumicounter. The transcription activity was expressed with the promoter activity of SV40 being set as 1. The results obtained are shown in FIGS. 5, 6 and 7. FIGS. 5 and 6 compare the transcription activity of Ad-IAI.3B-1816 in the established ovarian cancer cell lines (OC) with the transcription activity in the cervical cancer cell lines (CC) and the normal ovary cell lines (NOE). FIG. 7 compares the transcription activity of Ad-IAI.3B-1816 in the primary cultured ovarian cancer cell lines (pOC) with the transcription activity in the cervical cancer cell lines (CC) and the normal ovary cell lines (NOE). As can be seen from FIGS. 5, 6 and 7, the transcription activity of Ad-IAI.3B-1816 in the established ovarian cancer cell lines (OC) and the primary cultured ovarian cancer cell lines (pOC) is markedly higher than that in the cervical cancer cell lines (CC) and the normal ovary cell lines (NOE).

EXAMPLE 3

Figure 8:
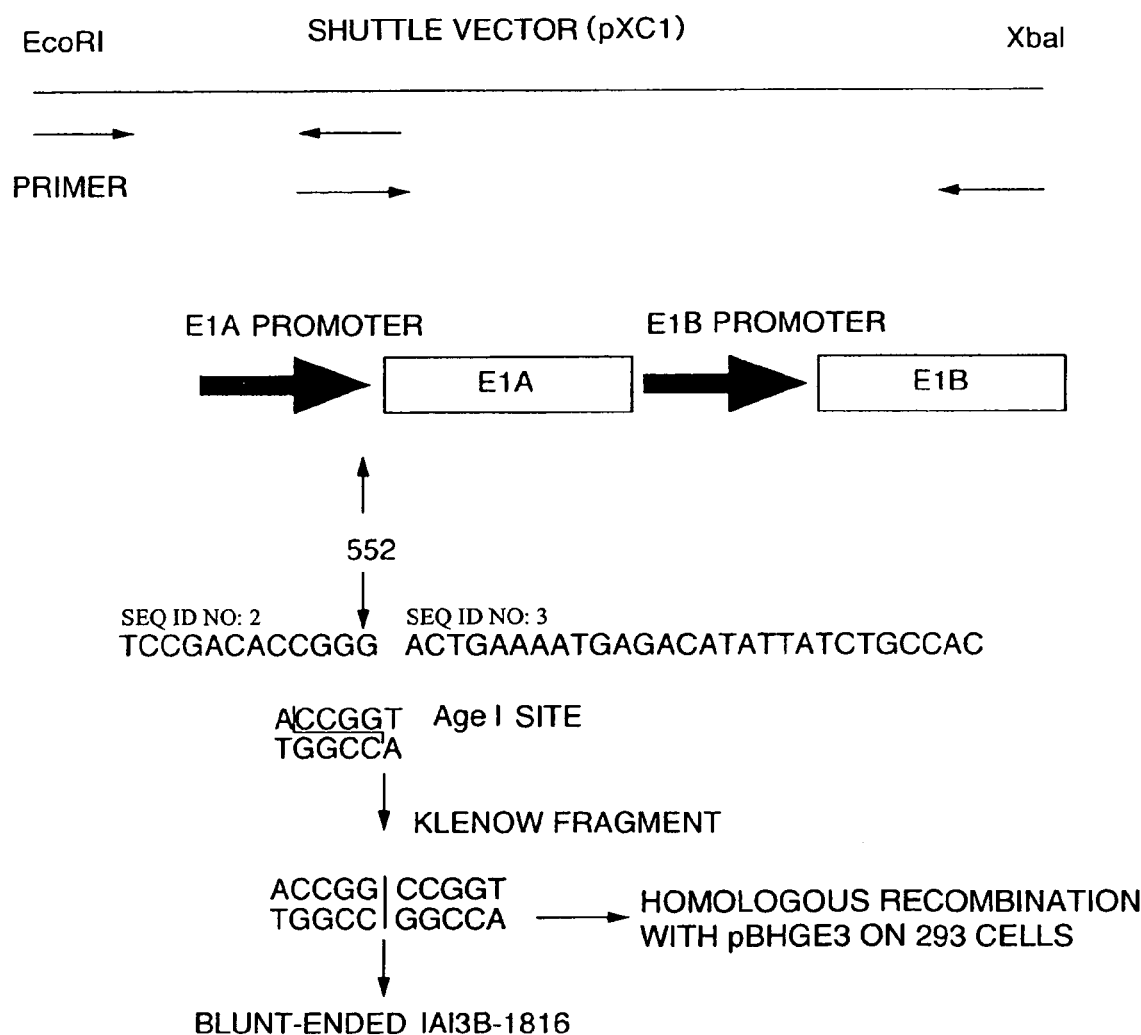
FIG. 8 is a drawing that shows a process of constructing an oncolystic adenovirus Ad-IAI.3B-1816 in which the 1816 bp deletion mutant of the promoter region of the IAI.3B gene has been inserted into the promoter region of the E1A gene.

Construction and Effect of Cytotoxic Tumor-Specific Adenovirus (1) Construction of Cytotoxic Tumor-Specific Adenovirus In order to create an oncolytic adenovirus with the IAI.3B gene promoter, T was inserted at a position of 552 bp of a shuttle vector pXC1 (Graham, F L et al., EMBO J. 3: 2917-2922, 1984) as shown in FIG. 8, and a AgeI site was introduced into this site, which was blunt-ended with a Klenow fragment, and to this site, IAI.3B-1816 (a 1816 bp base sequence at positions 1126-2941 set forth in SEQ ID NO: 1) that had been blunt-ended with a Klenow fragment was further inserted. This shuttle vector was subjected to homologous recombination with pBHGE3 (Graham, F L et al., EMBO J. 3: 2917-2922, 1984) to generate an oncolystic adenovirus Ad-IAI.3B-1816 in which a 1816 bp base sequence at positions 1126-2941 set forth in SEQ ID NO: 1 has been inserted into the E1A promoter region of adenovirus.

(2) Effect of Cytotoxic Tumor-Specific Adenovirus a) Proliferation Inhibitory Effect on Each Cell Line The proliferation inhibitory effect of the oncolytic adenovirus Ad-IAI.3B-1816 on an ovarian cancer cell line PA-1, a cervical cancer cell line SKGIIIA, a normal human ovary cell line NOE1 and a normal human keratinocyte cell line was examined. The culture condition for the ovarian cancer cell line and the cervical cancer cell line was 37° C. and 5% $CO_2$ in RPMI 1640 medium supplemented with 10% FCS. For the normal human ovary cell line and the normal human keratinocyte cell line, 5% FCS was added to the MCDB solution (Nissui) and cultured.

Figure 9:
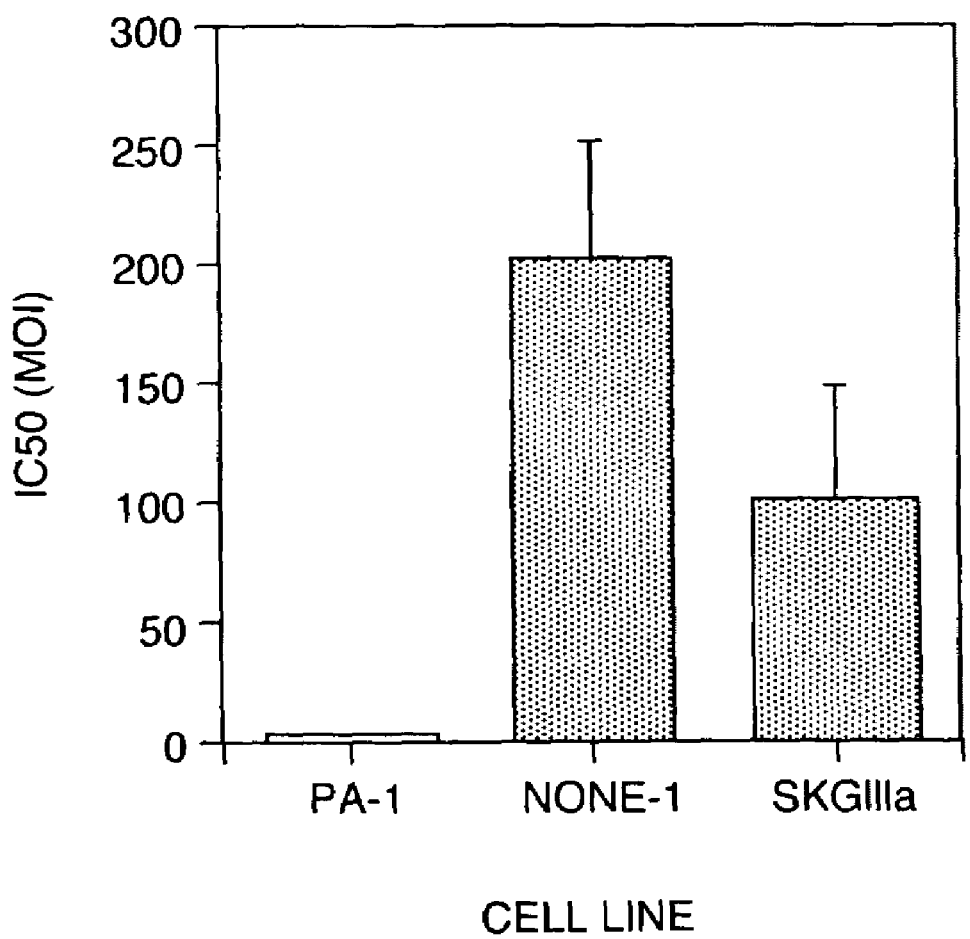
FIG. 9 is a graph showing the proliferation inhibitory effect to each cell line of the oncolystic adenovirus Ad-IAI.3B-1816.

The IC50 values obtained are shown in FIG. 9. IC50 for the ovarian cancer cell line PA-1 was 0.01 MOI, which is 20000 times that for the normal human ovary cell line NOE1 and 10000 times that for the cervical cancer cell line SKGIIIA.

From the foregoing, it was revealed that the oncolytic adenovirus Ad-IAI.3B-1816 having introduced therein a promoter comprising a 1816 bp base sequence at positions 1126-2941 set forth in SEQ ID NO: 1 has an anti-tumor effect specifically for ovarian cancer.

b) In vivo Anti-Tumor Activity

Figure 10:
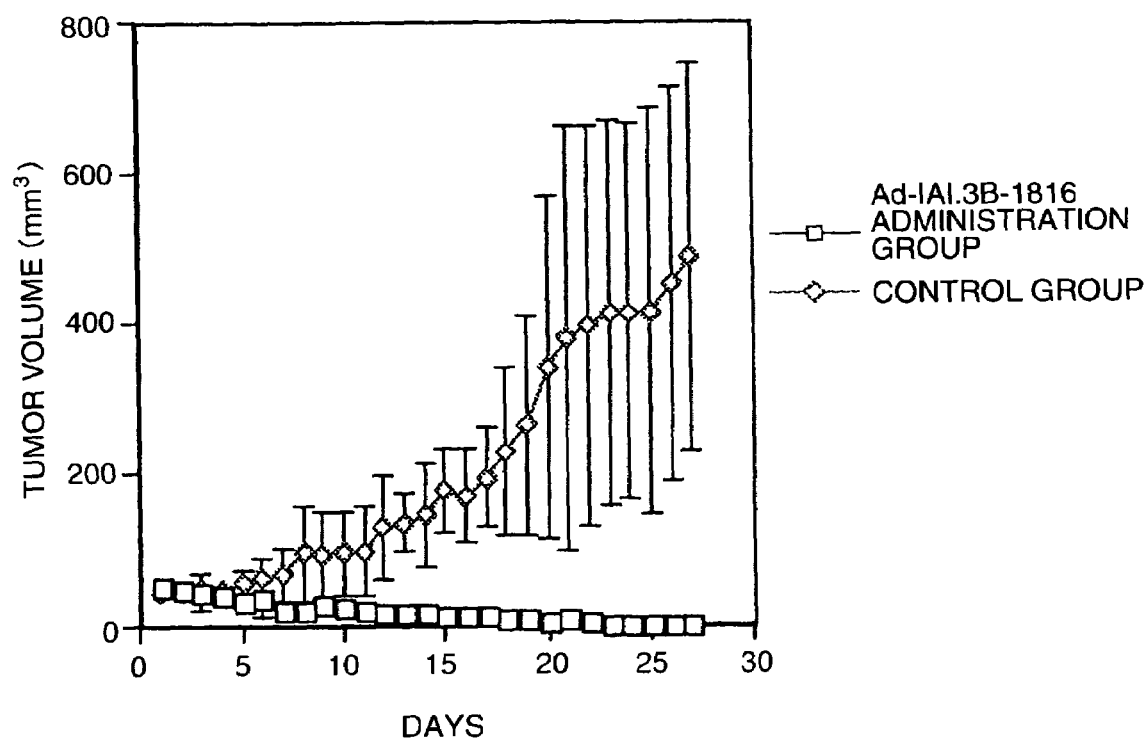
FIG. 10 is a graph showing the in vivo anti-tumor activity of the oncolystic adenovirus Ad-IAI.3B-1816.

The in vivo anti-tumor activity of the oncolytic adenovirus Ad-IAI.3B-1816 was examined. Thus, after the back of ten nude mice (6-week old) was inoculated subcutaneously with $1 \times 10^7$ cells of the ovarian cancer cell line PA-1, tumor size was examined, and when the diameter of tumor reached about 5 mm, they were divided into two groups. To only one group, $1 \times 10^{10}$ virus particles of the oncolytic adenovirus Ad-IAI.3B-1816 were injected into the inside of tumor for three times (day 1, 3 and 5). Then the size of tumor mass was measured with a caliper to determine the volume. The result obtained is shown in FIG. 10. As can be seen from the graph in FIG. 10, tumor began to regress immediately after the administration in the group (Ad-IAI.3B-1816 administration group) in which the oncolytic adenovirus Ad-IAI.3B-1816 was injected into the inside of tumor, and disappeared completely at day 20 of the administration and thereafter. In contrast, in the Ad-IAI.3B-1816 non-administration group (control group), the volume of tumor increased with days after the inoculation of PA-1.

Figure 11:
FIG. 11 is a photograph showing the in vivo anti-tumor activity of the oncolystic adenovirus Ad-IAI.3B-1816 in a nude mouse.

Also, FIG. 11 shows a photograph (left) of a nude mouse in the oncolytic adenovirus Ad-IAI.3B-1816 administration group at day 50 and a photograph (right) of a nude mouse in the control group at day 50. As compared to the tumor size of the control group, cancer has completely disappeared at the administration site (right dorsal part of the nude mouse on the left) of the nude mouse in the Ad-IAI.3B-1816 administration group.

c) In vitro Anti-Tumor Activity Against Each Cell Line

In a similar manner to the above a), the proliferation inhibitory effect of the oncolystic adenovirus Ad-IAI.3B-1816 on ovarian cancer cell lines, a cervical cancer cell line, normal human ovary cell lines and a normal human keratinocyte cell line was examined. The culture condition for the ovarian cancer cell lines and the cervical cancer cell line was 37° C. and 5% $CO_2$ in RPMI supplemented with 10% FCS. For the normal human ovary cell lines and the normal human keratinocyte cell line, 5% FCS was added to the MCDB solution (Nissui) and cultured. Culturing was started at 3000 cells/well (n=3) and IC50 values were determined after infection at each MOI. The results obtained are shown in Table 1. As can be seen from the results in Table 1, a high cytotoxic activity of the oncolystic adenovirus Ad-IAI.3B-1816 was noted only in ovarian cancer cell lines (PA-1, RMG-1, 420, OCC-1, OVCAR3, KK, KF, 429, DOV13 and MH).

TABLE 1 in vitro anti-tumor activity of the oncolystic adenovirus Ad-IAI.3B-1816

| Cell line | IC50 value (MOI) |
|---|---|
| Ovarian cancer cell line | |
| PA-1 | 0.014 |
| RMG-1 | 0.019 |
| 420 | 0.015 |
| OCC-1 | 0.02 |
| OVCA3 | 0.024 |
| KK | 0.1 |
| KF | 0.19 |

TABLE 1-continued in vitro anti-tumor activity of the oncolystic adenovirus Ad-IAI.3B-1816

| Cell line | IC50 value (MOI) |
|---|---|
| 429 | 0.884 |
| DOV13 | 0.858 |
| MH | 0.9 |
| Cervical cancer | |
| ME-180 | 170 |
| Normal human ovary cell line | |
| NOE-1 | 315.2 |
| NOE-2 | 104.91 |
| NOE-3 | 125.31 |
| Normal human keratinocyte | |
| K-42 | 342.9 | d) Synergistic Effect with Cisplatin

Figure 12:
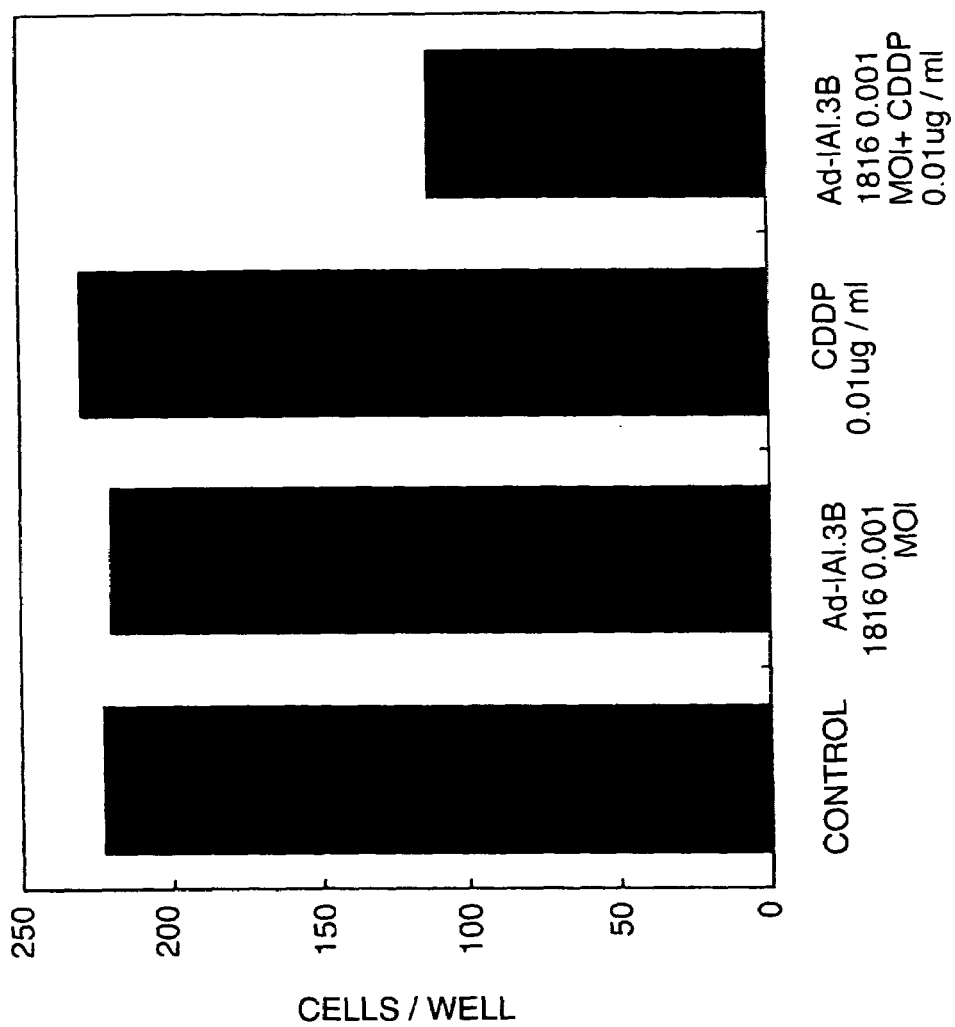
FIG. 12 is a graph showing an anti-cancer synergistic effect of the oncolystic adenovirus Ad-IAI.3B-1816 and cisplatin (CDDP).

Anti-cancer synergistic effect of the oncolystic adenovirus Ad-IAI.3B-1816 and cisplatin (CDDP) was investigated on a ovarian cancer cell line PA-1. Thus, PA-1 cells at 300 cells/well was plated onto a 12-well plate, and on the next day the oncolystic adenovirus Ad-IAI.3B-1816 or cisplatin was added and cultured for 9 days. The culture liquid was RPMI culture medium supplemented with 10% fetal calf serum and cultured at 37° C., 5% $CO_2$. After completion of culture, trypan blue staining was performed to determine the number of surviving cells, and IC50 of each proliferation inhibitory effect was calculated to examine the synergistic effect. The results obtained are shown in FIG. 12. As can be seen from FIG. 12, PA-1 did not undergo cytotoxicity when Ad-IAI.3B-1816 at MOI 0.001 and CDDP at 0.01 μg/ml were each acted on alone for 9 days. However, when the both are used in combination under this condition, the number of PA-1 cells decreased to less than half in the 9-day culture, confirming synergistic effect of the oncolystic adenovirus Ad-IAI.3B-1816 and cisplatin.

INDUSTRIAL APPLICABILITY

As can be seen from the above, the promoter activity of the IAI.3B gene is highest at 1816 bp upstream of the transcription initiation point, it is almost the same as the transcription activity of the CMV promoter in ovarian cancer cell lines, exhibits activity two to three times that of the SV40 promoter in cervical cancer cell lines, and the activity was low in normal ovary cells and keratinocytes with very low activity values at about 20 to 30% that of the SV40 promoter. Thus, the IAI.3B gene promoter has a specifically high specificity for ovarian cancer, and higher activity was also noted in other cancer cells as compared to normal cells. Also, with the oncolystic adenovirus generated according to the present invention, very high anti-tumor effect was noted in ovarian cancer cell lines, which makes it very promising as a therapeutic agent for ovarian cancer. The invention promoter can also be used for common E1-deleted or E1/E3-deleted adenovirus vector, and for gene therapy practiced in recent years with naked plasmid vector or gene therapy using ribosome. The ovarian cancer-specific gene expression by the tumor-specific promoter of the present invention can reduce side effects and permits administration at large doses, further enhancing the clinical usefulness of gene therapy.

The invention claimed is:

1. An isolated or synthesized polynucleotide sequence consisting of nucleotides 1126-2941 or 2501-2941 of SEQ ID NO: 1.

2. An isolated or synthesized polynucleotide sequence consisting of nucleotides 2626-2941, 2376-2941, 1251-2941, or 1001-2941 of SEQ ID NO: 1.

3. An isolated or synthesized polynucleotide sequence according to claim 1 or 2, wherein said isolated or synthesized polynucleotide sequence has ovarian cancer-specific promoter activity.

* * * * *

UNITED STATES PATENT AND TRADEMARK OFFICE
CERTIFICATE OF CORRECTION

| | | |
|---|---|---|
| PATENT NO. | : 7,321,030 B2 | |
| APPLICATION NO. | : 10/489258 | |
| DATED | : January 22, 2008 | |
| INVENTOR(S) | : Katsuyuki Hamada | |

It is certified that error appears in the above-identified patent and that said Letters Patent is hereby corrected as shown below:

Title page: Item (73) Assignee:

Delete "The New Industry Research Organization"

Insert -- GENE MEDICINE JAPAN, INC. --

Signed and Sealed this

Fourteenth Day of August, 2012

David J. Kappos
*Director of the United States Patent and Trademark Office*

SEQUENCE LISTING

<160> NUMBER OF SEQ ID NOS: 1

<210> SEQ ID NO 1
<211> LENGTH: 2941
<212> TYPE: DNA
<213> ORGANISM: Homo sapiens

<400> SEQUENCE: 1

| | | | | | |
|---|---|---|---|---|---|
| aaacatgtat | cttttaaaaa | ggtttagaaa | aatgacaact | tcattttatc | attttaaaat | 60 |
| aaggtaaatt | gggctgggcg | tcggtggctc | acgcctgtca | atcacagcac | ttagggaggc | 120 |
| cgaggcgggc | ggatgacctg | aggtcgggag | ttcaagacca | gcctgaccaa | tacggagaaa | 180 |
| cctcgtttct | actaaaaata | caaaaaaatg | agccaggcat | ggtggtgcat | gcgtgtaatc | 240 |
| ccagctactc | gggagctgag | gcaggagaat | cgcttgaacc | cacgagtcag | aggttgcggt | 300 |
| gagcccaaat | cacgccgatt | acactccagc | ctgggcaaca | agagcgaagc | tccgtctcaa | 360 |
| aaataaataa | aataaaataa | ggtaaattta | agatttggaa | ggttttagaa | taatacaaaa | 420 |
| tcctttaaag | gttctagaag | ttgcttttg | taattagaca | atataaattc | tgtatttttt | 480 |
| cacatattgc | ttccaaccct | ttgggtcttt | tcctttctcc | aagaaagaga | aagctacagg | 540 |
| ggagtgactg | accgggtaag | tggtgagctt | tctccaatgc | ttctggctgt | tttcttttc | 600 |
| ttgcataaaa | ccaaaatcaa | caacgaccaa | accaacacca | atcaaggcct | ccctgcccct | 660 |
| agcctttccc | agcgacccac | tctcatctca | ggatccccct | caagcacatc | cctgccggca | 720 |
| gcatctgtta | ctactgacgc | tcctctactt | ccctcttgcg | ctttctcaat | agcacaaatg | 780 |
| gatccagttc | ttaagttctc | cctcccacaa | aatcctgtct | cctcccttc | ccagacatat | 840 |
| tcctggcact | tcttcttccg | caagggccca | tcttctcata | tataccagcc | ggtgtttatt | 900 |
| tctttgtttg | tttttgagac | ggagtgtcgt | tctgccaccc | aggctggagt | gcaatggcgc | 960 |
| gatctcggct | cactgcaacc | tccgcctcct | gggttcaagc | gattctcctg | cctcagctcc | 1020 |
| tgagtagctg | gcgcgcgcca | ccacgcccgg | ctaattttg | tatttttagt | agagacgggg | 1080 |
| tttcaccacg | atggtcaggc | tggtctcgaa | ctcctgacct | cgtgatccat | ccgccttggc | 1140 |
| ctcccaaagt | gctaggaata | caggcgtaag | ccaccatccc | cggcgaccag | ctgatgttct | 1200 |
| tatacacatg | gtgtcccctt | caaggcacat | tccagttcct | atcaggagga | ttcctcctcg | 1260 |
| gacacactgt | gcccccaacc | tgatccttag | tgcttccctc | gagacctaca | aactgccccc | 1320 |
| ttccccgggg | ggttcacaac | gccttatgcc | tctcaggttc | cgccccgcc | cctcgcataa | 1380 |
| gaatacccat | ctgcctagct | tcggaaattc | actttccccc | gcccgtcccc | cggagcatcc | 1440 |
| cttgggcccc | tgtcccttc | ccggggctct | tctaccttaa | cccagagcag | agggtgcagg | 1500 |
| cctcctgagc | caggggccc | agttatctga | gaaacccac | ggcctgtccc | ccgtccagaa | 1560 |
| cgtctcagcg | agctcacgac | gcgcagtcac | gttttttcc | cccctctac | attgcagatg | 1620 |
| tggctcccaa | tgttgacgtt | ggccaggacc | tttgcaaaca | agccaggcca | aaaagtttca | 1680 |
| atatttacac | tggctgcttt | aataagggca | ttgatcttat | cctccgtaaa | ggtcacctca | 1740 |
| tagtcctgca | gaatgagggc | agagtagatg | caggcaagct | gggagacgga | ggccatagcg | 1800 |
| cgggcgagtg | tggggctggg | gctgccggac | gcggtgctac | tcaccggatg | aagtgagggt | 1860 |
| ctcaccccaa | cgcggcctta | gcttcctcgg | aaggaccgaa | caccttggcg | gcagccgagg | 1920 |
| aaagggttc | cacagttta | atttatctgt | aattcccacg | ctttactgtt | gccacgaaa | 1980 |
| ccgctgagca | atagcctctc | agaataggaa | atcaagcacac | agtcagagga | agggcgggac | 2040 |

```
                                                -continued agaaagagcc tagcatctct cggggctctg ggttggccac ccagtcctcc cctggtgaca   2100
taaaaagaaa gagacggaaa aggaagaatt ctacctgagt tcgccgtaaa gcgcccgccc   2160
tctcgcctct acgcttccag ttgcggctta ttacgtcaca gtaattgctg taccaaggtc   2220
agaatcgcca cctgaggcct gaatatcagc gtaagatagt gtccaaagca gtcttaagaa   2280
gaggtcccat tacccactc tttccgccct aatggaggtc tccagtttag gtaaataaaa    2340
ggattgttgg gaggtggagg gaaagaacta ctatttccaa catgcattgc ggaacgaaag   2400
gccttggcca cactgttcct tggaaactgt agtcttatgg agaggaacat ccaataccaa   2460
agcgggcaca attctcacgg aaatccagtg gatagattgg agacctccgc gggcttatac   2520
atgtcaacag taatggattg gagtgttgtt atgttctcct atcttgagag cagagactag   2580
gccaaaaaaa gatacctaca actcctagga agactacgat tcccatccag ccccacgagt   2640
ctcgggcaag tagtcctcta aggtcagtgg cctgcgggga cgcagtgggc gccgaatttg   2700
cctggggaag gggaaatccg ctctggccca catctgcgca ctcctagttc cgcccctcag   2760
cctcaatgtt tgttattgtt gttcgggttc aggttgcttc tgccccgccc catcgacgca   2820
atctccacca atcaatggcg tggtcgtttt gagggacaag tggtgagagc caatcatctt   2880
ggcgaacact cggagaaaca ggggactagt tactgtcttt atccgccatg ttagattcac   2940
c                                                                   2941
```